US008929512B2

(12) United States Patent
Kamitake

(10) Patent No.: US 8,929,512 B2
(45) Date of Patent: Jan. 6, 2015

(54) MOBILE TYPE RADIOGRAPHIC APPARATUS

(75) Inventor: Takahiro Kamitake, Sennan (JP)

(73) Assignee: Shimadzu Corporation, Kyoto (JP)

( * ) Notice: Subject to any disclaimer, the term of this patent is extended or adjusted under 35 U.S.C. 154(b) by 164 days.

(21) Appl. No.: 13/822,282

(22) PCT Filed: Apr. 13, 2011

(86) PCT No.: PCT/JP2011/002186
§ 371 (c)(1),
(2), (4) Date: Mar. 11, 2013

(87) PCT Pub. No.: WO2012/032688
PCT Pub. Date: Mar. 15, 2012

(65) Prior Publication Data
US 2013/0170619 A1 Jul. 4, 2013

(30) Foreign Application Priority Data
Sep. 10, 2010 (JP) .................. 2010-203296

(51) Int. Cl.
H05G 1/10 (2006.01)
A61B 6/00 (2006.01)
A61B 6/10 (2006.01)

(52) U.S. Cl.
CPC ............... *A61B 6/4405* (2013.01); *A61B 6/00* (2013.01); *A61B 6/102* (2013.01); *A61B 6/4233* (2013.01); *A61B 6/4452* (2013.01)
USPC ......................................... 378/102; 378/198

(58) Field of Classification Search
USPC .................... 378/209, 101, 102, 103, 198
See application file for complete search history.

(56) References Cited

U.S. PATENT DOCUMENTS

| 2004/0066899 | A1* | 4/2004 | Araki et al. ............... 378/102 |
| 2008/0095324 | A1 | 4/2008 | Watanabe |
| 2013/0064351 | A1* | 3/2013 | Urbon et al. ............. 378/98.5 |

FOREIGN PATENT DOCUMENTS

| CN | 101164497 A | 4/2008 |
| JP | 2006-043274 A | 2/2006 |
| JP | 2008-029644 A | 2/2008 |
| JP | 2008-259881 A | 10/2008 |

OTHER PUBLICATIONS

International Search Report issued in International Application No. PCT/JP2011/002186 mailed May 17, 2011.
Chinese Office Action dated Aug. 19, 2014 issued in Chinese Patent Application No. 201180042929.5.

* cited by examiner

*Primary Examiner* — Hoon Song
(74) *Attorney, Agent, or Firm* — McDermott Will & Emery LLP

(57) ABSTRACT

A mobile type radiographic apparatus is provided, which can inhibit damage to a detecting device as much as possible. This invention provides a storage holder for storing an FPD, and catches for fixing the FPD to the storage holder so that the FPD stored cannot be taken out of the storage holder. Further, this invention provides a carriage movement controller which, when a carriage is about to be moved while the FPD is not in a locked state, notifies the operator to that effect. Consequently, the operator will become aware of having forgotten to lock the FPD when moving the carriage. This construction assures that the FPD is in a fixed state, whereby the FPD is never damaged during traveling of the carriage.

6 Claims, 4 Drawing Sheets

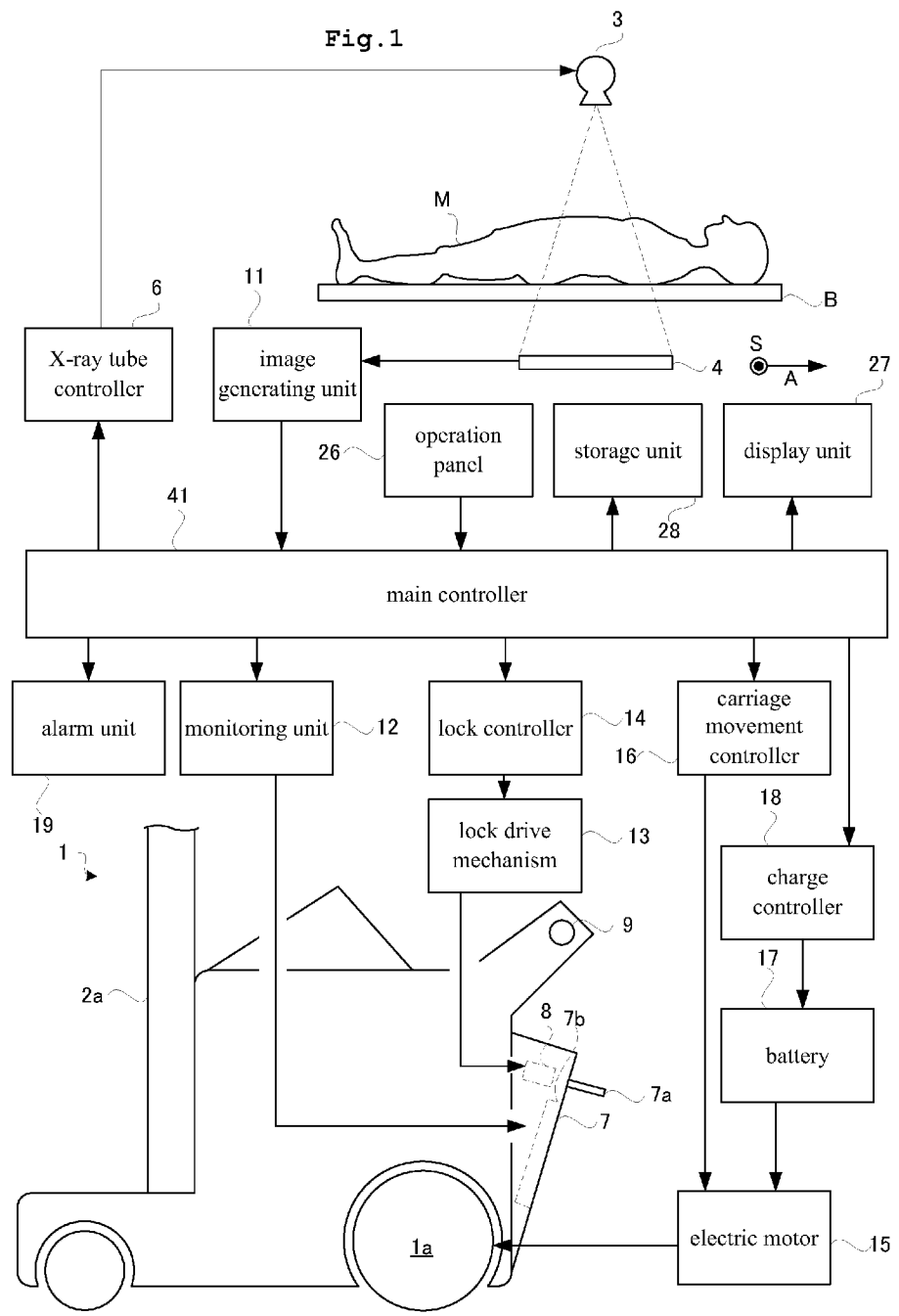

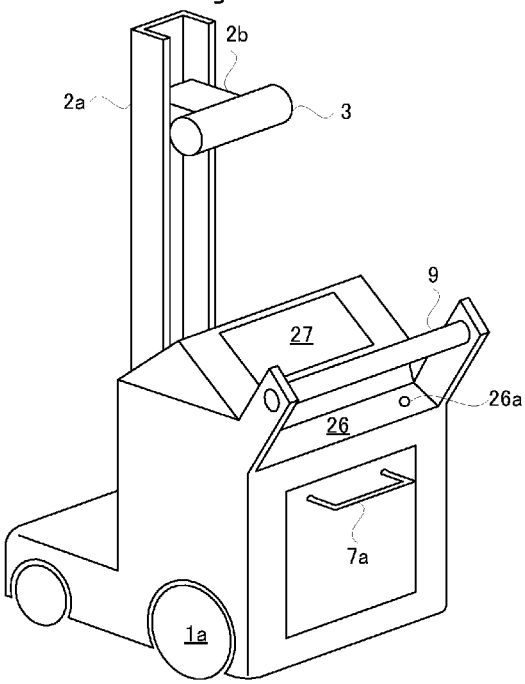
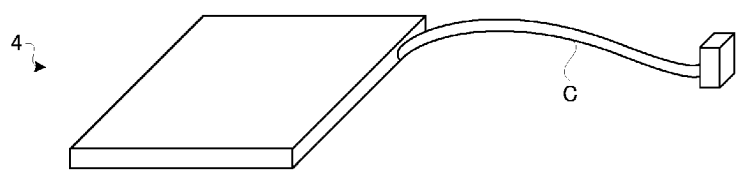
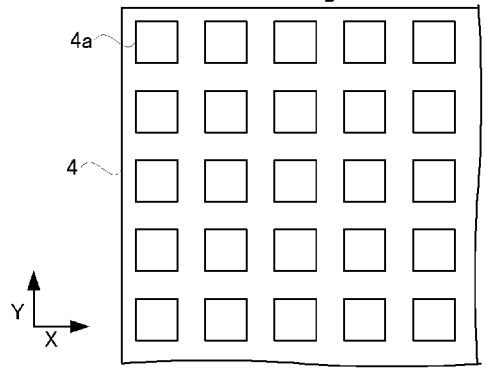

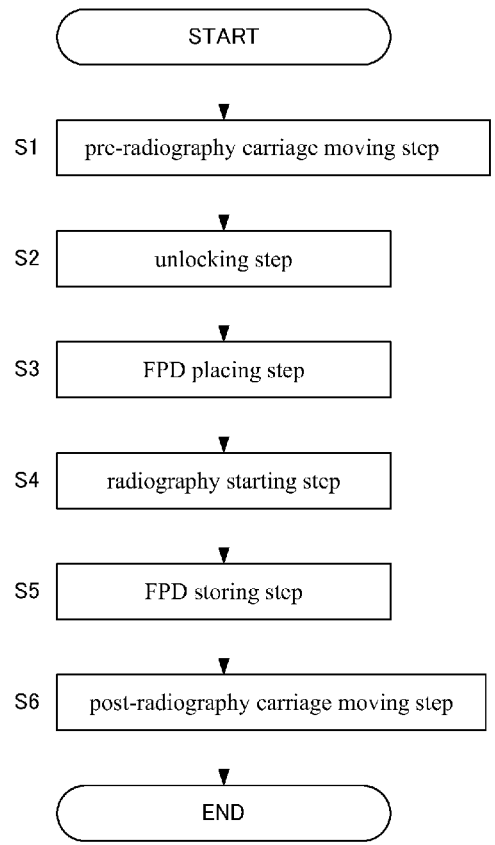
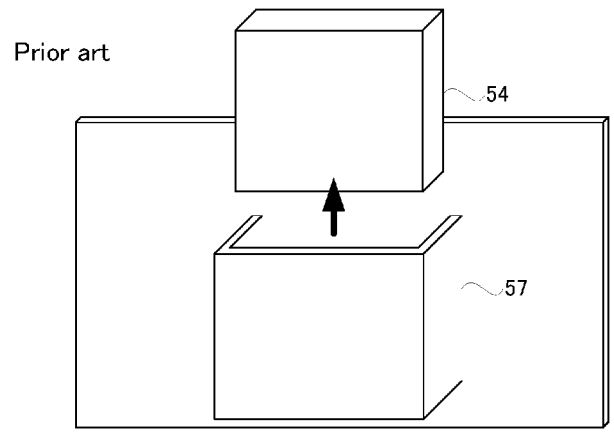

MOBILE TYPE RADIOGRAPHIC APPARATUS

RELATED APPLICATIONS

This application is the U.S. National Phase under 35 U.S.C. §371 of International Application No. PCT/JP2011/002186, filed on Apr. 13, 2011, which in turn claims the benefit of Japanese Application No. 2010-203296, filed on Sep. 10, 2010, the disclosures of which Applications are incorporated by reference herein.

TECHNICAL FIELD

This invention relates to a mobile type radiographic apparatus having a set of devices needed in radiography mounted on a carriage, and more particularly, relates to a mobile type radiographic apparatus devised so that a detecting device be not damaged.

BACKGROUND ART

Conventionally, a mobile type radiographic apparatus used in a medical institution has a set of devices needed in radiography mounted on an electrically movable carriage. Typical examples of the devices mounted on the carriage include a radiation source for emitting radiation toward a patient, a detecting device for detecting radiation transmitted through the patient, and an image generating device for imaging detection signals outputted from the detecting device (see Patent Document 1 and Patent Document 2).

A specific construction of the detecting device will be described. The detecting device in the conventional mobile type radiographic apparatus is constructed of a sheet type flat FPD (flat panel detector). This FPD has a plane of incidence for receiving radiation transmitted through a patient, and has a cable for outputting radiation detection signals to the image generating device.

When carrying out actual examination, the mobile type radiographic apparatus is first moved to the patient's room. Then, the patient is placed in a position between the radiation source and the FPD, and radiation is emitted from the radiation source to generate an image. When the examination is completed and the mobile type radiographic apparatus is to be moved, FPD 54 is first moved away from the patient and placed in a holder provided in a housing of the mobile type radiographic apparatus (see FIG. 7). As shown in FIG. 7, the holder 57 has a pocket which can receive the FPD 54 in an upstanding position with a radiation incidence direction extending horizontally.

When the operator pushes a lever provided on the mobile type radiographic apparatus after placing the FPD 54 in the holder 57, an internal driving device operates. Then, the mobile type radiographic apparatus proceeds in a direction in which the operator has pushed the lever, and leaves the patient's room.

[Patent Document 1] Unexamined Patent Publication No. 2008-259881
[Patent Document 2] Unexamined Patent Publication No. 2006-43274

DISCLOSURE OF THE INVENTION

Problem to be Solved by the Invention

However, the conventional construction has the following drawback.

That is, according to the conventional construction, the FPD 54 is not fixed to the holder 57, and when the mobile type radiographic apparatus were moved as it is, the FPD 54 would jounce inside the holder 57. If a situation should arise where the mobile type radiographic apparatus is further shaken in this state, the FPD 54 would in the worst case jump out of the holder 57 and drop to the floor of the patient's room.

The FPD 54 is a direct conversion type radiation detector having an amorphous selenium layer for converting radiation into charge carrier pairs. Since manufactured of a multiplex lamination of a semiconductor layer, an insulator layer and so on, this FPD 54 is susceptible to physical shocks. When a shock is added to the FPD 54, the layers constituting the FPD 54 will become detached, resulting in defective pixels or breakdown of the FPD 54.

The FPD 54 is expensive. It is therefore advantageous to use the FPD 54 for a long period of time by avoiding application of physical shocks as much as possible, thereby to hold down the maintenance cost of the mobile type radiographic apparatus.

This invention has been made having regard to the state of the art noted above, and its object is to provide a mobile type radiographic apparatus which can inhibit damage to a detecting device as much as possible.

Means for Solving the Problem

To fulfill the above object, this invention provides the following construction.

A mobile type radiographic apparatus according to this invention comprises a radiation source for emitting radiation; a radiation source control device for controlling the radiation source; a detecting device for detecting the radiation emitted and outputting detection signals; a carriage having, mounted thereon, the radiation source and the radiation source control device; a storage device mounted on the carriage for storing the detecting device; a lock device for fixing the detecting device stored to the storage device; a monitoring device for monitoring whether a locked state has been set to fix the detecting device to the storage device by setting a lock of the lock device; an input device for allowing an operator to input instructions to move the carriage; and a notifying device operable, when the instructions to move the carriage are made while the detecting device is not in the locked state, to notify the operator to that effect.

[Functions and effects] This invention provides a storage device for storing a detecting device, and a lock device for fixing the detecting device to the storage device so that the detecting device stored will not jounce inside the storage device. Consequently, even if the mobile type radiographic apparatus is shaken during traveling of the carriage, the detecting device will never jounce inside the storage device. Further, this invention provides a notifying device which, when the operator attempts to move the carriage with the detecting device not being in the locked state, notifies the operator to that effect. Consequently, when moving the carriage, the operator will become aware of having forgotten to lock the detecting device. With such a construction, the detecting device is reliably put in the fixed state, whereby the detecting device is never damaged during traveling of the carriage.

The above mobile type radiographic apparatus, preferably, comprises a power switch for controlling supply of electric power to the mobile type radiographic apparatus; a lock control device for controlling setting and releasing of the lock of the lock device; and a lock driving device for driving the lock device; wherein the lock control device instructs the lock driving device to set the lock when the power switch is turned OFF.

[Functions and effects] The above construction represents a more specific construction of the mobile type radiographic apparatus according to this invention. That is, when the power switch is turned OFF, the lock control device instructs the lock device to lock the detecting device. Consequently, the detecting device is in the locked state reliably fixed to the storage device when the power switch turned ON next time to use the mobile type radiographic apparatus. When using the mobile type radiographic apparatus, the apparatus is first moved to the patient, and the detecting device is not taken out of the storage device immediately after the power switch is turned ON. The above construction can prevent damage to the detecting device with increased reliability. Even if a shock occurs during storage of the mobile type radiographic apparatus to shake the apparatus, since the detecting device is in the locked state, the detecting device will not jounce inside the storage device.

The above mobile type radiographic apparatus, preferably, comprises an accumulating device for accumulating electric power; a carriage driving device for driving the carriage using the electric power accumulated in the accumulating device; a charge control device for controlling charging of the accumulating device; a lock control device for controlling setting and releasing of the lock of the lock device; and a lock driving device for driving the lock device; wherein the lock control device instructs the lock driving device to set the lock when the charge control device starts charging of the accumulating device.

[Functions and effects] The above construction represents a more specific construction of the mobile type radiographic apparatus according to this invention. That is, when charging of the accumulating device is started, the lock control device will instruct the lock device to lock the detecting device. Consequently, the detecting device is in the locked state reliably fixed to the storage device when the mobile type radiographic apparatus is used after the charging is completed. The apparatus is first moved to the patient immediately after completion of the charging, and the detecting device is not taken out of the storage device immediately after completion of the charging. The above construction can prevent damage to the detecting device with increased reliability.

The above mobile type radiographic apparatus, preferably, comprises a plurality of detecting devices; a plurality of storage devices for storing the respective detecting devices separately; a plurality of lock devices provided for the respective storage devices; and a plurality of lock driving devices provided for the respective lock devices; wherein the lock control device, when a certain detecting device is taken out of the storage device, instructs the respective lock driving devices to set the lock so that the detecting devices other than the taken-out detecting device cannot be taken out of the storage devices; and wherein the lock control device, when a certain detecting device is stored in the storage device, instructs the respective lock driving devices to cancel the lock so that the respective detecting devices can be taken out of the storage devices.

[Functions and effects] The above construction represents a more specific construction of the mobile type radiographic apparatus according to this invention. That is, the lock control device, when a certain detecting device is taken out of the storage device, instructs the respective lock devices to set the lock so that the detecting devices other than the taken-out detecting device cannot be taken out of the storage devices. This can prevent a different detecting device from being taken out of the apparatus by mistake, leaving one of the detecting devices outside the apparatus. Thus, where the apparatus has a plurality of detecting devices mounted thereon, when the operator carries out a radiographic operation, forgetting that one of the detecting devices has been taken out, there will arise an increased possibility of dropping the forgotten detecting device to the floor during the operation. Since the above construction does not allow a plurality of detecting devices to be taken out at a time, the operator is prevented from continuing a radiographic operation while leaving a detecting device lying about.

In the above mobile type radiographic apparatus, preferably, the notifying device acts as a carriage movement control device for inhibiting movement of the carriage.

[Functions and effects] The above construction represents a more specific construction of the mobile type radiographic apparatus according to this invention. With the notifying device acting as a carriage movement control device, the operator can easily notice that the detecting device is not locked.

In the above mobile type radiographic apparatus, preferably, the notifying device acts as an alarm device for giving a warning tone.

[Functions and effects] The above construction represents a more specific construction of the mobile type radiographic apparatus according to this invention. With the notifying device acting as an alarm device, the operator can easily notice that the detecting device is not locked.

Effects of the Invention

This invention provides a storage device for storing a detecting device, and a lock device for fixing the detecting device to the storage device so that the detecting device stored will not jounce inside the storage device. Further, this invention provides a notifying device which, when an attempt is made to move the carriage with the detecting device not being in the locked state, notifies the operator to that effect. Consequently, when moving the carriage, the operator will become aware of having forgotten to lock the detecting device. With such a construction, the detecting device is reliably put in the fixed state, whereby the detecting device is never damaged during traveling of the carriage.

BRIEF DESCRIPTION OF THE DRAWINGS

FIG. 1 is a functional block diagram illustrating a construction of a mobile type radiographic apparatus according to Embodiment 1;

FIG. 2 is a perspective view illustrating the construction of the mobile type radiographic apparatus according to Embodiment 1;

FIG. 3 is a perspective view illustrating a construction of an FPD according to Embodiment 1;

FIG. 4 is a plan view illustrating the construction of the FPD according to Embodiment 1;

FIG. 6 is a flow chart illustrating operation of the mobile type radiographic apparatus according to Embodiment 1; and FIG. 7 is a perspective view illustrating a construction of a conventional mobile type radiographic apparatus.

Figure 5:
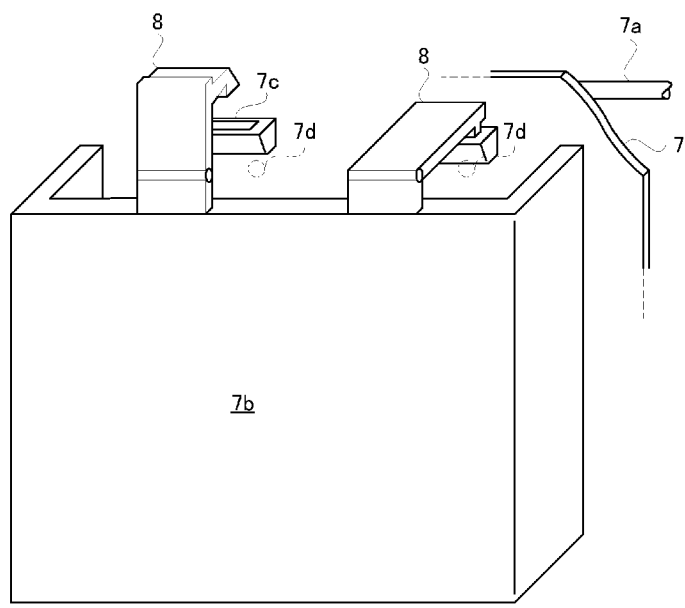
FIG. 5 is a perspective view illustrating a construction of a storage holder according to Embodiment 1.

DESCRIPTION OF REFERENCES 1 carriage
3 X-ray tube (radiation source)

4 FPD (detecting device)
6 X-ray tube controller (radiation source control device)
7 storage holder (storage device)
8 catches (lock device)
9 lever (input device)
12 monitoring unit (monitoring device)
13 lock drive mechanism (lock driving device)
14 lock controller (lock control device)
15 electric motor (carriage driving device)
16 carriage movement controller (notifying device, carriage movement control device)
17 battery (accumulating device)
18 charge controller (charge control device)
19 alarm unit (notifying device, alarm device)
26a power switch

BEST MODE FOR CARRYING OUT THE INVENTION

The best mode of this invention will be described hereinafter.
[Embodiment 1]
One embodiment of the mobile type X-ray apparatus of this invention will be described hereinafter. FIG. 1 is a block diagram showing a construction of a control system of the mobile type X-ray apparatus according to the embodiment of this invention. FIG. 2 is a perspective view showing an appearance of the apparatus in the embodiment. FIG. 3 is a perspective view showing a flat panel type X-ray detector (X-ray image receiving device) provided on the apparatus in the embodiment. FIG. 4 is a plan view showing an arrangement of X-ray detecting elements in the flat panel type X-ray detector of the apparatus in the embodiment. X-rays are an example of the radiation in this invention, and FPD is an abbreviation of flat panel detector.

The mobile type X-ray apparatus in the embodiment, as shown in FIGS. 1 and 2, has, mounted on a movable carriage 1 of the four wheel type and rear wheel drive type, a required set of equipment such as an X-ray tube 3, to start with, which emits X-rays to a patient M to be radiographed, a flat panel type X-ray detector (hereinafter abbreviated as "FPD" as appropriate) 4 of the direct conversion type which detects transmission X-ray images of the patient M, and an X-ray tube controller 6 which controls the X-ray tube 3. Thus, the apparatus in the embodiment is constructed to be able, by movement of the carriage 1, to travel and go to the patient's room where the patient M to be radiographed lies. The X-ray tube 3 corresponds to the radiation source in this invention, and the X-ray tube controller 6 corresponds to the radiation source control device in this invention.

That is, the apparatus in the embodiment is the type capable of what is called round visit radiography, which can perform X-raying while the patient M remains in the patient's room instead of going out to an X-ray room.

The X-ray tube 3 is, as shown in FIG. 2, attached to a distal end of a holding arm 2b vertically movably attached in a horizontal state to a strut 2a erected vertically on a front part of the carriage 1. The strut 2a is rotatable about a central axis as a rotation axis while maintaining the upright state. During traveling of the carriage 1, the X-ray tube 3 is located along with the holding arm 2b rearward of the strut 2a so that the X-ray tube 3 will not hinder the traveling. At a time of radiography, the strut 2a is rotated to locate the X-ray tube 3 along with the holding arm 2b forward of the strut 2a. And adjustment is made as necessary to move the holding arm 2b up and down along the strut 2a so that the X-ray tube 3 may be set to a suitable height.

The FPD 4 is a plate-like device as shown in FIG. 3, and has an electric cable C for outputting detection signals to the body of the carriage, and inputting control signals from the body of the carriage. This FPD 4 detects emitted X-rays and outputs the detection signals. The FPD 4 is usually stored inside the carriage 1, is taken out before radiography, and is placed below the patient M. At this time, the FPD 4 and carriage 1 are electrically connected through the electric cable C. The FPD 4 corresponds to the detecting device in this invention.

The construction of FPD 4 will be described. The FPD 4 is, as shown in FIG. 4, a two-dimensional X-ray detector with numerous X-ray detecting elements 4a arranged in a matrix pattern (in XY directions) on an X-ray detecting plane which receives X-rays, and is constructed to detect transmitted X-ray images projected to the X-ray detecting plane which are converted by the X-ray detecting elements 4a into electric signals as detection signals for X-ray image acquisition. This FPD 4 is a direct conversion type X-ray imaging device, and is formed by laminating an amorphous selenium layer and numerous other layers.

The FPD 4 taken out of the storage holder 7 provided on the carriage 1 is, as shown in FIG. 1, set to a radiographing position below the patient M lying on a bed B. The FPD 4 is connected to the electric cable C for collecting the detection signals between the carriage 1 and FPD 4. The storage holder 7 corresponds to the storage device in this invention.

As shown in FIG. 1, the storage holder 7 is provided in form of a drawer on a rear side of the carriage 1, and the FPD 4 necessary for X-raying is stored therein ready to be taken out. When taking the FPD 4 out of the storage holder 7, the operator pulls a pull handle 7a shown in FIG. 1 and exposes a pocket 7b provided inside the carriage, and then holds the FPD 4 and takes it out by hand. When putting and lodging the FPD 4 in the storage holder 7 also, the pull handle 7a is pulled to expose the pocket 7b and put the FPD 4 inside.

A specific construction of the storage holder 7 will be described. As shown in FIG. 5, the storage holder 7 has the pocket 7b for receiving the FPD 4, which is formed on the back surface as seen from the pull handle 7a. Seen from the operator, this pocket 7b is provided in the interior of the mobile type radiographic apparatus, and is drawn from the interior of the carriage 1 when the operator pulls the pull handle 7a. This pocket 7b has an opening directed vertically upward, through which the FPD 4 is inserted vertically downward. When the FPD 4 is inserted into this opening, the FPD 4 will contact the bottom of the pocket 7b for support. The opening of the pocket 7b is formed long and narrow in accordance with the shape of the FPD 4 seen from a direction perpendicular to the incident direction of X-rays incident on the FPD 4.

Two catches 8 are arranged in the opening of the pocket 7b in a way to occlude the opening. The catches 8 are shaped to straddle the long and narrow opening of the pocket 7b in the transverse direction. The catches 8 have hinges, and these hinges allow distal ends of the catches 8 to move toward the pull handle 7a and, conversely, to move away therefrom. On the other hand, the proximal ends of the catches 8 are fixed to the top end of the pocket 7b. When the operator bends the catches 8, the opening of the pocket 7b is closed and it becomes impossible to fetch the FPD 4 from inside the pocket 7b. When the operator extends the catches 8, the opening of the pocket 7b is opened and the FPD 4 inside the pocket 7b can be taken out. In FIG. 5, the left one of the two catches 8 is bent, and the right one is in an upstanding state with the bending canceled. When the catches 8 are bent, the distal ends immerse in holes 7c formed in the storage holder 7, and the bent state of the catches 8 is maintained by contact between the distal ends of the catches 8 and the holes 7c. The catches 8 correspond to the lock device in this invention.

A locking state in the construction of Embodiment 1 will be described. The locking state of Embodiment 1 refers to a state where the FPD 4 stored in the pocket 7b of the storage holder 7 is prohibited from moving from the pocket 7b and the FPD 4 is fixed to the storage holder 7. That is, in the locking state, the two catches 8 provided for the pocket 7b are in the bent state to close the opening of the pocket 7b. Even if an attempt is made to take out the FPD 4 stored in this state, the catches 8 will obstruct the takeout action. Thus, the catches 8 fix the FPD 4 to the storage holder 7 in such a way that the stored FPD 4 will not jounce in the interior of the storage holder 7. The FPD 4 at the time of locking state is fixed to the pocket 7b through contact with the two catches 8 to be thereby pressed. Therefore, even if the carriage 1 is shaken in the locking state, the FPD 4 will never jounce in the interior of the pocket 7b.

A monitoring unit 12 is provided in order to monitor sequentially whether the catches 8 are in the above locking state. That is, the storage holder 7 has sensors 7d for detecting whether the distal ends of the catch 8 are immersed in the holes 7c of the storage holder 7, and the monitoring unit 12 monitors based on outputs of these sensors 7d whether the catches 8 are in the locking state. The monitoring unit 12 corresponds to the monitoring device in this invention.

A lock drive mechanism 13 is provided for driving the catches 8 to bend and extend them in order to realize the locking state and unlocking state. A lock controller 14 controls this. That is, the lock controller 14 outputs signals of locking and unlocking instructions to the lock drive mechanism 13. Thus, the mobile type radiographic apparatus according to Embodiment 1 can set the lock through manual bending of the catches 8 and can also set the lock automatically through the lock controller 14. The lock drive mechanism 13 corresponds to the lock driving device in this invention. The lock controller 14 corresponds to the lock control device in this invention.

On the one hand, the carriage 1 has, arranged on upper surfaces thereof, a display unit 27 for displaying information and data required for X-raying, and an operation panel 26 for conducting controls required for X-raying and carriage movement (see FIG. 2). The display unit 27 is constructed to display on its screen control menus, X-ray images and so on according to the contents of controls on the operation panel 26 and progress of X-raying. The operation panel 26 includes a power switch 26a which controls electric power supply to the mobile type radiographic apparatus (see FIG. 2). When this power switch 26a is set to OFF, the electric power supply to each component of the entire mobile type radiographic apparatus is cut off, and the power source of the mobile type radiographic apparatus will be in OFF state.

The X-ray tube controller 6 which performs control required for X-raying causes the X-ray tube 3 to emit X-rays according to X-raying conditions such as a tube voltage and a tube current determined prior to X-raying execution. The mobile type radiographic apparatus according to Embodiment 1 includes an image generating unit 11 for acquiring an X-ray image corresponding to a transmitted X-ray image of the patient M based on the detection signals outputted from the FPD 4.

In the case of the apparatus in the embodiment, the carriage 1 is constructed electrically movable. That is, in response to driving control performed by the operator on the operation panel 26, the carriage 1 travels with rotation of rear wheels 1a thereof as a carriage movement controller 16 rotates an electric motor 15. The electric motor 15 corresponds to the carriage driving device in this invention, and the carriage movement controller 16 corresponds to the notifying device and the carriage movement control device in this invention.

A battery 17 is provided in order to accumulate electric power and supply the electric power to the electric motor 15. A charge controller 18 controls charging of the battery 17 and supplies electric power to the battery 17 at a charging time. The electric motor 15 drives the carriage 1 using the electric power accumulated in the battery 17. The battery 17 corresponds to the accumulating device in this invention, and the charge controller 18 corresponds to the charge control device in this invention.

The carriage 1 includes a lever 9 for use by the operator. When the operator pushes this lever 9, the carriage movement controller 16 will detect this, and control the rear wheels 1a to move the carriage 1 in the direction in which the lever 9 was pushed. That is, the lever 9 serves as an input device for allowing the operator to input instructions to move the carriage 1. The lever 9 corresponds to the input device in this invention.

An alarm unit 19 gives a sound (warning tone) when an abnormality occurs to the mobile type radiographic apparatus. The alarm unit 19 corresponds to the notifying device and the alarm device in this invention.

A main controller 41 is provided in order to perform overall control of the respective controllers. This main controller 41 is formed of a CPU, and the components 6, 11, 12, 14, 16 and 18 are realized by executing various programs, or the above components may be divided into arithmetic units in charge thereof to be executed. A storage unit 28 stores all of the various parameters relating to radiography.

<Operation of Mobile Type Radiographic Apparatus>

Next, operation of the mobile type radiographic apparatus will be described. To radiograph the patient M with the mobile type radiographic apparatus in Embodiment 1, as shown in FIG. 6, the carriage 1 is first moved (pre-radiography carriage moving step S1), and the lock fixing the FPD 4 is undone (unlocking step S2). Then, the FPD 4 is taken out of the storage holder 7 and placed below the patient M (FPD placing step S3), and X-raying is started (radiography starting step S4). After the radiography, the FPD 4 is put into the storage holder 7 (FPD storing step S5), and the carriage 1 is moved again (post-radiography carriage moving step S6). These steps will be described in order hereinafter.

<Pre-Radiography Carriage Moving Step S1>

The operator operates the lever 9 to move the carriage 1 to the room of the patient M. That is, the carriage movement controller 16 detects the operation of the lever 9 by the operator, and drives the electric motor 15 in compliance with the operation. This assists in the movement of the carriage 1, and the operator can move the carriage 1 without applying strong force to the lever 9. Since the FPD 4 is in the locked state at this time, the FPD 4 stored in the storage holder 7 is fixed to the storage holder 7. Therefore, even if the carriage 1 is shaken by the movement, the FPD 4 will never jounce in the interior of the storage holder 7.

<Unlocking Step S2>

After the movement of the carriage 1, the operator pulls the pull handle 7a of the storage holder 7 to expose the pocket 7b located in the carriage 1. Then, the operator raises the two catches 8 to cancel the locked state of the FPD 4.

<FPD Placing Step S3>

The operator takes out of the storage holder 7 the FPD 4 which has become available for takeout, and sets it below the bed B of the patient M as shown in FIG. 1. Then, the operator operates the operation panel 26 to move the X-ray tube 3 above the patient M. This will result in the patient M being in a position between the X-ray tube 3 and FPD 4.

<Radiography Starting Step S4>

When the operator operates the operation panel 26 and gives instructions to start X-raying, the X-ray tube controller 6 reads set values relating to control of the X-ray tube 3 such as a tube voltage, a tube current and a pulse width stored in the storage unit 28. The X-ray tube controller 6 controls the X-ray tube 3 according to these set values, and causes the X-ray tube 3 to emit X-rays. X-rays transmitted through the patient M are detected by the FPD 4, and the detection signals at this time are outputted to the image generating unit 11 through the electric cable C. The image generating unit 11 generates an X-ray fluoroscopic image showing a fluoroscopic image of the patient M based on the detection signals.

<FPD Storing Step S5>

After completion of the radiography, the FPD 4 is moved away from the patient M and inserted into the pocket 7b of the storage holder 7. After inserting the FPD 4, the operator bends the two catches 8 to fix the FPD 4 to the pocket 7b. Consequently, when the carriage 1 moves, the FPD 4 will not jounce inside the pocket 7b. In this state, the operator pushes the pull handle 7a of the storage holder 7 to put the pocket 7b in the interior of the carriage 1.

Such operation of the operator is appropriate as use of the mobile type radiographic apparatus. However, for the purpose of describing the construction of this embodiment, description will be made hereinafter of the case where the operator has forgotten to bend the two catches 8. That is, it is assumed that the pocket 7b has been placed in the interior of the carriage 1 in the unlocked state of the FPD 4 which has been inserted in the pocket 7b but not fixed to the pocket 7b.

<Post-Radiography Carriage Moving Step S6>

The monitoring unit 12 constantly continues monitoring the locked state of the FPD 4 through the sensors 7d. In the above description of operation, the monitoring unit 12 detects in step S1 that the FPD 4 is in the locked state, and detects in subsequent steps S2-S5 detects that the FPD 4 is not in the locked state. The monitoring unit 12 successively outputs data showing this state of the lock to the carriage movement controller 16.

The carriage movement controller 16 continues detecting operations of the lever 9 by the operator. The carriage movement controller 16 will not operate the electric motor 15 when the operator operates the lever 9 to give instructions to move the carriage 1 while the FPD 4 is not in the locked state. Then, the operator notices that, in spite of the application of pressure to the lever 9, no assistance is exerted by the electric motor 15. This operation is the most characteristic of the construction in this embodiment. Consequently, the operator becomes aware of having started movement of the carriage 1 with the FPD 4 not being in the locked state. In this way, when instructions to move the carriage 1 are made while the FPD 4 is not in the locked state, the carriage movement controller 16 will notify the operator to that effect. Thus, the carriage movement controller 16 acts as the carriage movement control device to inhibit movement of the carriage 1 in the unlocked state of the FPD 4.

As the construction of the carriage movement controller 16, it is not necessarily limited to the construction for not operating the electric motor 15. For example, by inhibiting the electric power outputted to the electric motor 15, the operator may be notified of an absence of the assistance by the electric motor 15. The carriage movement controller 16, along with the above operation, may output a signal to the display unit 27 to indicate on the screen of the display unit 27 that the FPD 4 is not locked.

Having noticed that the FPD 4 is not locked, the operator puts the FPD 4 in the locked state by manually bending the catches 8, or by operating the operation panel 26 to give instructions to the lock controller 14 for causing the lock drive mechanism 13 to bend the catches 8, and applies pressure to the lever 9 again. Then, the carriage movement controller 16 operates the electric motor 15 as in the conventional construction, whereby the electric motor 15 provides assistance.

When the FPD 4 is not inserted in the pocket 7b, the monitoring unit 12 determines that the FPD 4 is not in the locked state even if the catches 8 are in the bent state. Therefore, also when the operator has forgotten to insert the FPD 4 in the pocket 7b, the assistance by the electric motor 15 is not provided. Therefore, the carriage movement controller 16 can notify the operator of having forgotten to store the FPD 4.

The operator operates the lever 9, after the FPD 4 is put in the locked state, to move the carriage 1 out of the room of the patient M. Since the FPD 4 is in the locked state at this time, the FPD 4 stored in the storage holder 7 is fixed to the storage holder 7. Therefore, even if the carriage 1 is shaken by the movement, the FPD 4 never jounces inside the storage holder 7.

As described above, the construction in Embodiment 1 includes the storage holder 7 for storing the FPD 4, and the catches 8 for fixing the FPD 4 to the storage holder 7 so that the FPD 4 stored will not jounce inside the storage holder 7. Consequently, even if the mobile type radiographic apparatus is shaken during traveling of the carriage 1, the FPD 4 will never jounce inside the storage holder 7. Further, the construction in Embodiment 1 includes the carriage movement controller 16 which, when the operator attempts to move the carriage 1 with the FPD 4 not being in the locked state, notifies the operator to that effect. Consequently, when moving the carriage 1, the operator will become aware of having forgotten to lock the FPD 4. With such a construction, the FPD 4 is reliably put in the fixed state, whereby the FPD 4 is never damaged during traveling of the carriage 1.

This invention is not limited to the foregoing construction, but may be modified as follows.

(1) In addition to the construction described hereinbefore, the lock controller 14 may be adapted operable in response to an operation of the power switch 26a by the operator. That is, when the power switch 26a is turned OFF by the operator, this is notified to the lock controller 14 from the operation panel 26. The lock controller 14 instructs the lock drive mechanism 13 to set the lock. On this instruction, the lock drive mechanism 13 bends the catches 8 to place the FPD 4 in the locked state. Consequently, the FPD 4 is in the locked state reliably fixed to the storage holder 7 when the power switch 26a is turned ON next time to use the mobile type radiographic apparatus. When using the mobile type radiographic apparatus, the apparatus is first moved to the patient M, and the FPD 4 is not taken out of the storage holder 7 immediately after the power switch 26a is turned ON. Thus, this invention can prevent damage to the FPD 4 with increased reliability. Even if a shock occurs during storage of the mobile type radiographic apparatus to shake the apparatus, since the FPD 4 is in the locked state, the FPD 4 will not jounce inside the storage holder 7.

(2) In addition to the construction described hereinbefore, the lock controller 14 may be adapted operable in response to an operation of the charge controller 18 to start charging. That is, the charge controller 18, when charging of the battery 17 is started, will notify the lock controller 14 to that effect. The lock controller 14 will instruct the lock drive mechanism 13 to set the lock. On this instruction, the lock drive mechanism 13 bends the catches 8 to place the FPD 4 in the locked state. Consequently, the FPD 4 is in the locked state reliably fixed to the storage holder 7 when the mobile type radiographic apparatus is used after the charging is completed. The apparatus is first moved to the patient M immediately after completion of the charging, and the FPD 4 is not taken out of the storage holder 7 immediately after completion of the charging. Thus, the above construction can prevent damage to the FPD 4 with increased reliability.

(3) In addition to the construction described hereinbefore, this invention may be adapted to a construction which can store a plurality of FPDs 4. That is, the mobile type radiographic apparatus includes a plurality of FPDs 4, a plurality of storage holders 7 (pockets 7b, sensors 7d) for storing these individually, a plurality of catches 8 provided for each of the storage holders 7, and a plurality of lock drive mechanisms 13 provided for the respective catches 8. The monitoring unit 12 monitors each FPD 4. Following information outputted from the monitoring unit 12, the lock controller 14, when a certain FPD 4 is taken out of the storage holder 7 by the operator, instructs a plurality of lock drive mechanisms 13 to set the lock so that the FPDs 4 other than that FPD 4 cannot be taken out of the storage holders 7. On this instruction, the lock drive mechanisms 13 bend the catches 8 to place the respective FPDs 4 in the locked state.

This can prevent a different FPD 4 from being taken out of the apparatus by mistake, leaving one of the FPDs 4 outside the apparatus. Thus, in the construction in which the apparatus carries a plurality of FPDs 4, when the operator carries out a radiographic operation, forgetting that one of the FPDs 4 has been taken out, there will arise an increased possibility of dropping the forgotten FPD 4 to the floor during the operation. Since the above construction does not allow a plurality of FPDs 4 to be taken out at a time, the operator is prevented from continuing a radiographic operation while leaving an FPD 4 lying about.

Following the information outputted from the monitoring unit 12, the lock controller 14, when the operator stores the FPD 4 taken out previously in the storage holder 7, instructs the plurality of lock drive mechanisms 13 to cancel the lock so that each of the FPDs 4 having been in the locked state can be taken out of the storage holders 7. On this instruction, the lock drive mechanisms 13 extend the catches 8 to place the respective FPDs 4 in the unlocked state. In this way, the operator can easily take an unlocked FPD 4 out of the storage holder 7.

(4) In addition to the construction described hereinbefore, the monitoring unit 12 may be constructed successively to output data showing lock states to the alarm unit 19. The carriage movement controller 16 continues detecting operation of the lever 9 by the operator. And the carriage movement controller 16 outputs a start of operation of the lever 9 by the operator to the alarm unit 19.

And when the operator operates the lever 9 with the FPD 4 not in the locked state, instructing for movement of the carriage 1, the alarm unit 19 will emit a warning tone. Then, the operator notices that the carriage 1 has been started moving while the FPD 4 is in the unlocked state. In this construction, the alarm unit 19 acts as the notifying device in this invention.

(5) While the foregoing embodiment provides the medical apparatus, this invention is applicable also to industrial and nuclear apparatus.

(6) The X-rays in the foregoing embodiment are one example of the radiation in this invention. Therefore, this invention can be adapted also for radiation other than X-rays.

[Industrial Utility]

This invention is suitable for a medical radiographic apparatus.

The invention claimed is:

1. A mobile type radiographic apparatus comprising:
a radiation source for emitting radiation;
a radiation source control device for controlling the radiation source;
a detecting device for detecting the radiation emitted and outputting detection signals;
a carriage having, mounted thereon, the radiation source and the radiation source control device;
a storage device mounted on the carriage for storing the detecting device;
a lock device for fixing the detecting device stored to the storage device;
a monitoring device for monitoring whether a locked state has been set to fix the detecting device to the storage device by setting a lock of the lock device;
an input device for allowing an operator to input instructions to move the carriage; and
a notifying device operable, when the instructions to move the carriage are made while the detecting device is not in the locked state, to notify the operator to that effect.

2. The mobile type radiographic apparatus according to claim 1, comprising:
a power switch for controlling supply of electric power to the mobile type radiographic apparatus;
a lock control device for controlling setting and releasing of the lock of the lock device; and
a lock driving device for driving the lock device;
wherein the lock control device instructs the lock driving device to set the lock when the power switch is turned OFF.

3. The mobile type radiographic apparatus according to claim 1, comprising:
an accumulating device for accumulating electric power;
a carriage driving device for driving the carriage using the electric power accumulated in the accumulating device;
a charge control device for controlling charging of the accumulating device;
a lock control device for controlling setting and releasing of the lock of the lock device; and
a lock driving device for driving the lock device;
wherein the lock control device instructs the lock driving device to set the lock when the charge control device starts charging of the accumulating device.

4. The mobile type radiographic apparatus according to claim 2, comprising:
a plurality of detecting devices;
a plurality of storage devices for storing the respective detecting devices separately;
a plurality of lock devices provided for the respective storage devices; and
a plurality of lock driving devices provided for the respective lock devices;
wherein the lock control device, when a certain detecting device is taken out of the storage device, instructs the respective lock driving devices to set the lock so that the detecting devices other than the taken-out detecting device cannot be taken out of the storage devices; and
wherein the lock control device, when a certain detecting device is stored in the storage device, instructs the respective lock driving devices to cancel the lock so that the respective detecting devices can be taken out of the storage devices.

5. The mobile type radiographic apparatus according to claim 1, wherein the notifying device acts as a carriage movement control device for inhibiting movement of the carriage.

6. The mobile type radiographic apparatus according to claim 1, wherein the notifying device acts as an alarm device for giving a warning tone.

* * * * *